(12) United States Patent
Little et al.

(10) Patent No.: US 7,921,575 B2
(45) Date of Patent: Apr. 12, 2011

(54) METHOD AND SYSTEM FOR INTEGRATING ULTRASOUND INSPECTION (UT) WITH A COORDINATE MEASURING MACHINE (CMM)

(75) Inventors: Francis Howard Little, Cincinnati, OH (US); Yanyan Wu, Schenectady, NY (US); Jian Li, Rexford, NY (US); Nicholas J. Kray, Blue Ash, OH (US)

(73) Assignee: General Electric Company, Schenectady, NY (US)

( * ) Notice: Subject to any disclaimer, the term of this patent is extended or adjusted under 35 U.S.C. 154(b) by 130 days.

(21) Appl. No.: 11/964,939

(22) Filed: Dec. 27, 2007

(65) Prior Publication Data
US 2009/0165317 A1 Jul. 2, 2009

(51) Int. Cl.
*G01N 29/265* (2006.01)
*G01B 5/008* (2006.01)

(52) U.S. Cl. .............. 33/503; 33/556; 702/167; 73/602; 73/620; 73/627; 73/633

(58) Field of Classification Search .......... 600/443–448; 33/503, 556–561; 73/602, 620–629, 633; 702/167–168
See application file for complete search history.

(56) References Cited

U.S. PATENT DOCUMENTS

| | | | |
|---|---|---|---|
| 4,457,311 A * | 7/1984 | Sorenson et al. | 600/447 |
| 4,458,689 A * | 7/1984 | Sorenson et al. | 600/447 |
| 5,319,445 A | 6/1994 | Fitts | |
| 5,335,547 A * | 8/1994 | Nakajima et al. | 73/622 |
| 5,412,880 A * | 5/1995 | Raab | 33/503 |
| 5,521,847 A | 5/1996 | Ostrowski et al. | |
| 5,801,312 A | 9/1998 | Lorraine et al. | |
| 5,963,882 A * | 10/1999 | Viertl et al. | 702/39 |
| 6,254,540 B1 * | 7/2001 | Kikuchi et al. | 600/443 |
| 6,698,291 B2 * | 3/2004 | Yamamoto et al. | 73/620 |
| 7,228,642 B2 | 6/2007 | Enderle et al. | |
| 7,308,828 B2 | 12/2007 | Hashimoto | |
| 7,337,673 B2 * | 3/2008 | Kennedy et al. | 73/633 |
| 7,640,810 B2 * | 1/2010 | Kennedy et al. | 73/634 |
| 7,640,811 B2 * | 1/2010 | Kennedy et al. | 73/634 |
| 7,691,062 B2 * | 4/2010 | Kozak et al. | 600/443 |
| 2002/0128790 A1 | 9/2002 | Woodmansee | |
| 2007/0220767 A1 | 9/2007 | Pettersson | |
| 2007/0256862 A1 | 11/2007 | Lund et al. | |
| 2007/0261259 A1 | 11/2007 | Eaton | |
| 2008/0033295 A1 | 2/2008 | Matsumura | |
| 2008/0033298 A1 | 2/2008 | Habu et al. | |
| 2009/0178482 A1 * | 7/2009 | Hough et al. | 73/596 |

FOREIGN PATENT DOCUMENTS

WO 2007028941 A1 3/2007

* cited by examiner

*Primary Examiner* — Randy W Gibson
(74) *Attorney, Agent, or Firm* — William Scott Andes, Esq.; Armstrong Teasdale LLP

(57) ABSTRACT

A method is provided for assembling a measurement device for use in measuring a machine component. The method includes providing a coordinate measuring machine (CMM). The method also includes combining ultrasonic inspection (UT) capabilities and CMM capabilities to form an inspection probe. The inspection probe is installed on the CMM so that the inspection probe measures external boundaries of the machine component with the CMM capabilities and substantially simultaneously measures internal boundaries of the machine component with the UT capabilities.

20 Claims, 2 Drawing Sheets

METHOD AND SYSTEM FOR INTEGRATING ULTRASOUND INSPECTION (UT) WITH A COORDINATE MEASURING MACHINE (CMM)

BACKGROUND OF THE INVENTION

The field of the present invention relates generally to measurement probes, and more specifically, to a method of assembling a measurement probe for use in measuring a machine component.

Prior to being placed in service, at least some known rotor blades or other parts with internal geometry or with narrow openings are measured using measurement probes to ensure that that the blade has the proper dimensions for use in a turbine engine. Often, known blades are inspected via a non-destructive inspection technique to ensure that each blade does not include internal defects and/or cracks that are not visible to the naked eye. Accordingly, it is generally important to measure both the external and internal geometry of the blade.

Known methods for measuring a blade require two separate processes to inspect both the internal and external geometry of the blade. First, at least some known blades are inspected using one of computed tomography (CT) and/or ultrasonic tomography (UT) to inspect the internal geometry of the blade. A coordinate measuring machine (CMM) probe is then utilized to inspect the external geometry of the blade. Accordingly, a significant amount of time may be required to complete the setup and inspection process for each individual process of CT, CMM, and UT. Moreover, UT inspection currently requires a robotic arm and, therefore, requires a pre-inspection process to program the arm to accurately follow the contour of the blade.

Accordingly, known methods are generally time-consuming, not suitable for in-situ inspection, and/or expensive. Further, for CMM, a complicated blade geometry, such as a component having a deep, narrow opening or cavity, requires complicated setups and/or bending of the CMM probes to measure the cavity geometry. Moreover, for a compressor blade, the CMM probe must travel across both the pressure and suction sides of the blade. In addition, the CMM probe must compensate for CAD models and/or dense point measurements. However, probe compensation is generally a computationally complicated process.

BRIEF DESCRIPTION OF THE INVENTION

In one aspect, a method is provided for assembling a measurement device for use in measuring a machine component. The method includes providing a coordinate measuring machine (CMM). The method also includes combining ultrasonic inspection (UT) capabilities and CMM capabilities to form an inspection probe. The inspection probe is installed on the CMM so that the inspection probe measures external boundaries of the machine component with the CMM capabilities and substantially simultaneously measures internal boundaries of the machine component with the UT capabilities.

In another aspect, a measurement device is provided. The measuring device includes a coordinate measuring machine (CMM) and an inspection probe that combines ultrasonic inspection (UT) capabilities and CMM capabilities. The inspection probe is installed on the CMM so that the inspection probe measures external boundaries of a machine component with the CMM capabilities and substantially simultaneously measures internal boundaries of the machine component with the UT capabilities.

In yet another aspect, a system is provided for measuring a machine component. The system includes a measurement device including a coordinate measuring machine (CMM) and an inspection probe that combines ultrasonic inspection (UT) capabilities and CMM capabilities. The inspection probe installed on the CMM so that the inspection probe measures external boundaries of a machine component with the CMM capabilities and substantially simultaneously measures internal boundaries of the machine component with the UT capabilities. The system also includes a display that is coupled to the measurement device to facilitate displaying measurements of the machine component.

DETAILED DESCRIPTION OF THE INVENTION

An exemplary embodiment of the invention provides a system for measuring a machine component, such as, but not limited to, a blade. The system includes a measurement probe for measuring the machine component and a display for displaying measurements of the machine component. The measurement probe includes a coordinate measuring machine (CMM) probe coupled to an ultrasonic probe. The ultrasonic probe measures a position of at least one internal defect, such as a crack, within the machine component and represents a position of each internal defect with coordinates determined by the CMM probe. In another embodiment, the measurement probe may be a customized inspection probe that includes an ultrasonic probe installed on a CMM machine and having both ultrasonic capabilities and CMM capabilities. In such an embodiment, the ultrasonic probe is not physically coupled to the CMM probe. In any embodiment, the measurement probe combines the capabilities of ultrasonic inspection and CMM inspection.

In one embodiment, the measurement probe is configured to simultaneously measure a geometry of at least two sides of the machine component by placing the measurement probe in contact with one of the at least two sides. In another embodiment, the customized ultrasonic probe is configured to measure a surface that is substantially normal to the machine component. In the exemplary embodiment, the measurement probe is configured to measure a geometry of a rotor blade.

It should be noted that although the present invention is described with respect to rotor blades, one of ordinary skill in the art should understand that the present invention is not limited to being used only with rotor blades. Rather, the present invention may be used to measure any machine component.

Figure 1:
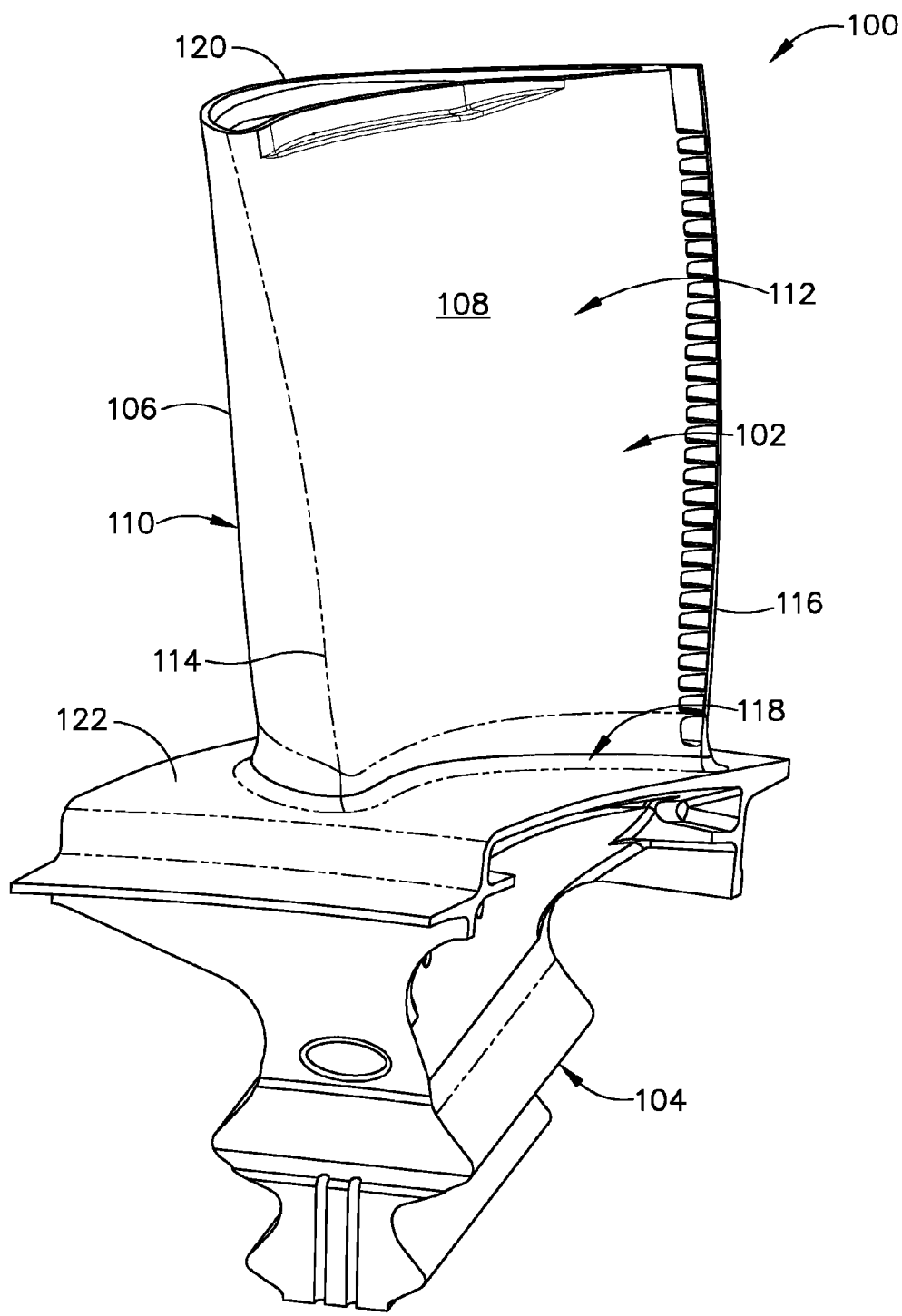
FIG. 1 is an exemplary embodiment of a turbine engine rotor blade.

FIG. 1 is an exemplary embodiment of a turbine engine rotor blade 100. Blade 100 includes an airfoil 102 and an integral dovetail 104 that is used for mounting blade 100 to a rotor (not shown). Blade 100 includes a first contoured sidewall 106 and a second contoured sidewall 108. In the exemplary embodiment, first sidewall 106 is convex and defines a suction side 110 of blade 100, and second sidewall 108 is concave and defines a pressure side 112 of blade 100. Sidewalls 106 and 108 are joined together at a leading edge 114 and at an axially-spaced trailing edge 116 of blade 100. More specifically, airfoil trailing edge 116 is spaced chordwise and downstream from airfoil leading edge 114. First and second sidewalls 106 and 108, respectively, extend longitudinally or radially outward in span from a blade root 118 positioned adjacent dovetail 104, to an airfoil or blade tip 120. A dovetail platform 122 is positioned at blade root 118 and extends radially outward from first and second sidewalls 106 and 108, respectively. It should be noted that blade 100 is exemplary only and the general configuration of blade 100 may take any conventional form, with or without platform 122 or dovetail 104. For example, blade 100 may be formed integrally with a disk in a blisk-type configuration that does not include dovetail 104.

Prior to installing blade 100 within an engine (not shown), and/or during maintenance of the engine, blade 100 is typically inspected using a measurement probe (not shown in FIG. 1) to ensure that that blade 100 is fabricated for and includes the proper dimensions for use in the engine. Further, blade 100 is inspected to ensure that blade 100 does not include internal and/or external defects. Accordingly, during this inspection, it is important to measure both the external and internal geometry of the blade.

Figure 2:
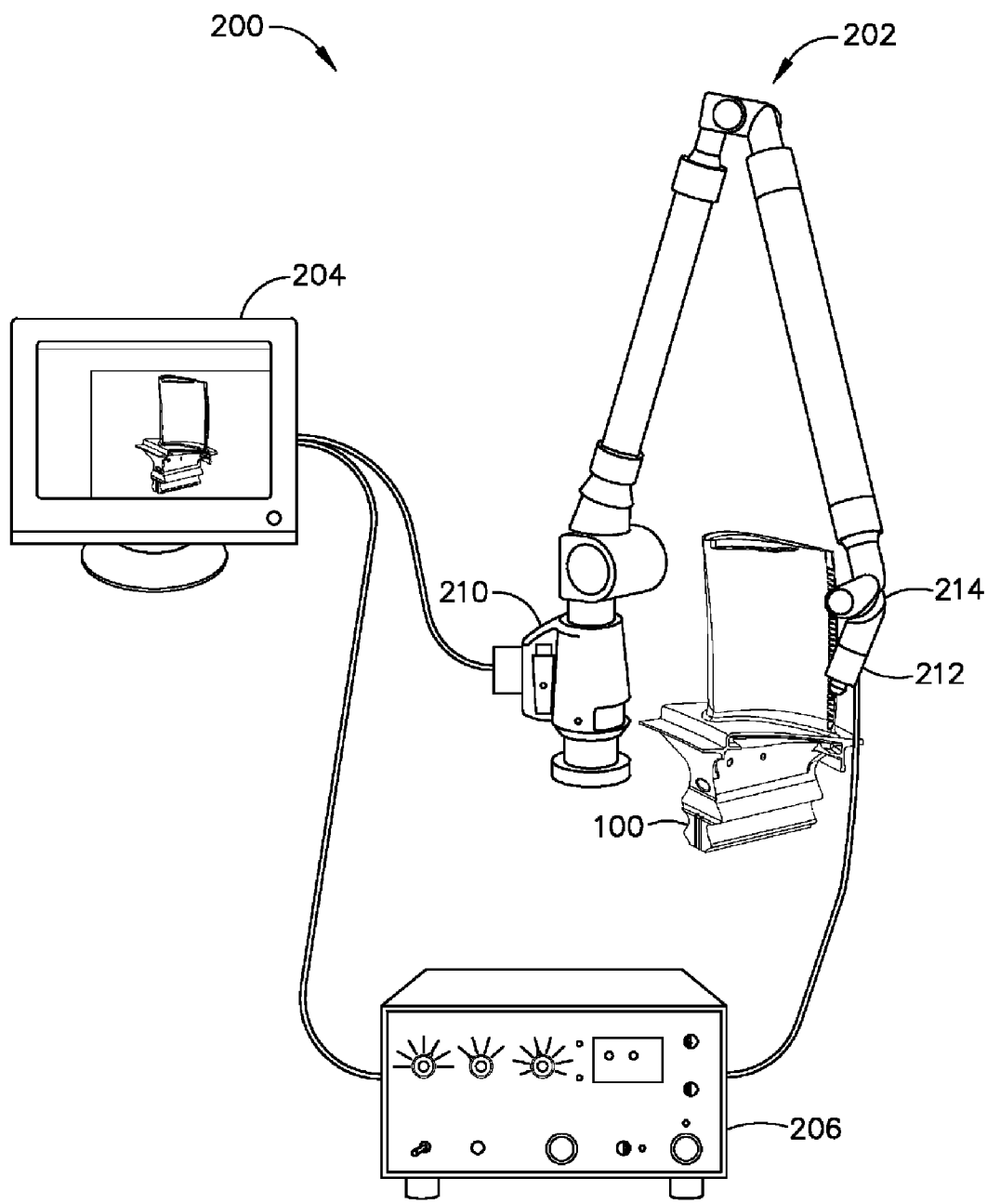
FIG. 2 is an illustration of an exemplary system that may be used to measure the rotor blade shown in FIG. 1.

FIG. 2 is an illustration of an exemplary system 200 that may be used to measure blade 100. In the exemplary embodiment, system 200 includes a measurement probe 202, a display 204, and an ultrasonic pulse receiver 206. Further, in the exemplary embodiment, measurement probe 202 includes a coordinate measuring machine (CMM) 210 and an ultrasonic probe 212. Ultrasonic probe 212 is coupled to a CMM probe 214 such that CMM probe 214 and ultrasonic probe 212 can measure, substantially simultaneously, the same location or substantially the same location relative to blade 100. Although the exemplary embodiment is described with respect to measurement probe 202 including an ultrasonic probe 212 coupled to a CMM probe 214, in an alternative embodiment, measurement probe 202 may be a customized inspection probe including an ultrasonic probe installed on CMM machine 210 and having both ultrasonic capabilities and CMM capabilities without physically coupling an ultrasonic probe 212 to a CMM probe 214. In any embodiment, measurement probe 202 combines the capabilities of ultrasonic inspection and CMM inspection. Further, in the exemplary embodiment, each component of system 200 is electrically coupled to a computer (not shown) and/or processor (not shown).

Ultrasonic probe 212 is electrically coupled to ultrasonic pulse receiver 206, which is electrically coupled to display 204. In one embodiment, ultrasonic probe 212 is also coupled to a signal digitizer (not shown). CMM 210 is also electrically coupled to display 204. Accordingly measurements received by both CMM probe 214 and ultrasonic probe 212 and/or the customized inspection probe can be displayed substantially simultaneously on display 204.

During operation, measurement probe 202 is used to inspect blade 100 by receiving measurements from CMM machine 210 and ultrasonic probe 212 substantially simultaneously. During inspection, CMM machine 210 is used to determine a position of ultrasonic probe 212 in terms of X,Y,Z coordinates. Substantially simultaneously, ultrasonic probe 212 is used to determine a thickness of blade 100 and/or a position of any internal defects within blade 100 by transmitting ultrasonic pulses to ultrasonic pulse receiver 206. In the exemplary embodiment, the thickness of the blade includes, but is not limited to, the distance between the suction side 110 (shown in FIG. 1) and pressure side 112 (shown in FIG. 1) of blade 100 and/or the distance between the leading edge 114 (shown in FIG. 1) and the trailing edge 116 (shown in FIG. 1) of blade 100. Accordingly, in the exemplary embodiment, the thickness and/or position as measured by ultrasonic probe 212 is combined with X,Y,Z coordinate information as determined by CMM probe 214. As such, the external boundaries and dimensions of blade 100, the internal boundaries and dimensions of blade 100, and any internal defects within blades 100 are displayed at real-time during the inspection process on display 204. In one embodiment, the boundaries, dimensions, and defects are displayed in real-time 3-dimensional imaging.

During operation, system 200 eliminates a need to position CMM probe 214 within deep and narrow cavities of blade 100. Rather, the cavity geometry is measured from an external surface of blade 100 using measurement probe 202. Further, in the exemplary embodiment, measurement probe 202 is only required to travel along either the pressure side 112 or the suction side 110 of blade 100 to measure the complete blade geometry on both sides. Accordingly, an amount of time required for the measurement is reduced. Moreover, the signal from ultrasonic probe 212 is sensitive to surface normal. Accordingly, the surface normal as measured by ultrasonic probe 212 can be used as a reference of surface normality for CMM probe 214.

In one embodiment, a method is provided for assembling a measurement device for use in measuring a machine component. The method includes providing a coordinate measuring machine (CMM). The method also includes combining ultrasonic inspection (UT) capabilities and CMM capabilities to form an inspection probe. The inspection probe is installed on the CMM so that the inspection probe measures external boundaries of the machine component with the CMM capabilities and substantially simultaneously measures internal boundaries of the machine component with the UT capabilities. In the exemplary embodiment, the measurement probe is coupled to a display to facilitate displaying measurements of the machine component.

In one embodiment, the inspection probe is configured to determine a position of at least one internal defect within the machine component using the UT capabilities. In another embodiment, the inspection probe is configured to determine coordinates of the inspection probe using the CMM capabilities, and represent the position of the at least one internal defect with the determined coordinates. In one embodiment, the inspection probe is configured to measure a geometry of at least two sides of the machine component by placing the measurement probe in contact with one of the at least two sides. In another embodiment, the inspection probe is configured to measure a surface that is substantially normal to the machine component. In the exemplary embodiment, the inspection probe is configured to measure a geometry of a rotor blade.

The above-described systems and methods facilitate providing a more timely and accurate inspection of both the external and internal structures of a machine component. The above-described systems and methods also facilitate the generation of real-time 3-dimensional imaging and the accurate acquisition of defect information of the machine component. Accordingly CMM productivity is improved, especially when measuring complicated geometries. Further, the above-described systems and methods facilitate providing simple probe compensation for the CMM with an ultrasonic sensor. Accordingly, the CMM has an increased capability of making internal measurements.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments of systems and methods for assembling a measurement probe are described above in detail. The systems and methods illustrated are not limited to the specific embodiments described herein, but rather, components of the system may be utilized independently and separately from other components described herein. Further, steps described in the method may be utilized independently and separately from other steps described herein.

While the invention has been described in terms of various specific embodiments, it will be recognized that the invention can be practiced with modification within the spirit and scope of the claims.

What is claimed is:

1. A method for assembling a measurement device for use in measuring a machine component, said method comprising:
   providing a coordinate measuring machine (CMM);
   combining ultrasonic inspection (UT) capabilities and CMM capabilities to form an inspection probe; and
   installing the inspection probe on the CMM so that the inspection probe measures external boundaries of the machine component with the CMM capabilities and substantially simultaneously measures internal boundaries of the machine component and a surface normal with the UT capabilities, wherein the surface normal is used as a reference of surface normality for the CMM capabilities.

2. A method in accordance with claim 1, further comprising determining a position of at least one internal crack within the machine component using the UT capabilities.

3. A method in accordance with claim 2, further comprising:
   determining coordinates of the inspection probe using the CMM capabilities; and
   representing the position of the at least one internal crack with the determined coordinates.

4. A method in accordance with claim 1, further comprising measuring a geometry of a rotor blade using the inspection probe.

5. A method in accordance with claim 1, further comprising measuring a geometry of at least two sides of the machine component by placing the inspection probe in contact with only one of the at least two sides to be measured.

6. A method in accordance with claim 1, further comprising displaying measurements of the machine component.

7. A measurement device comprising:
   a coordinate measuring machine (CMM); and
   an inspection probe that combines ultrasonic inspection (UT) capabilities and CMM capabilities, said inspection probe installed on the CMM so that the inspection probe measures external boundaries of a machine component with the CMM capabilities and substantially simultaneously measures internal boundaries of the machine component and a surface normal with the UT capabilities, wherein the surface normal is used as a reference of surface normality for the CMM capabilities.

8. A measurement device in accordance with claim 7, wherein a position of at least one internal defect within the machine component is measured using the UT capabilities.

9. A measurement device in accordance with claim 8, wherein:
   coordinates of the inspection probe are determined using the CMM capabilities; and
   the position of the at least one internal defect is represented with the determined coordinates.

10. A measurement device in accordance with claim 7, wherein said inspection probe is configured to measure a geometry of a rotor blade.

11. A measurement device in accordance with claim 7, wherein said inspection probe is configured to measure a geometry of at least two sides of the machine component when placed in contact with one of the at least two sides.

12. A measurement device in accordance with claim 7, wherein said inspection probe is configured to measure a surface that is substantially normal to the machine component.

13. A measurement device in accordance with claim 7, wherein said measurement device is coupled to a display to facilitate displaying measurements of the machine component.

14. A system for measuring a machine component, said system comprising:
   a measurement device comprising:
      a coordinate measuring machine (CMM); and
      an inspection probe that combines ultrasonic inspection (UT) capabilities and CMM capabilities, said inspection probe installed on the CMM so that the inspection probe measures external boundaries of a machine component with the CMM capabilities and substantially simultaneously measures internal boundaries of the machine component and a surface normal with the UT capabilities, wherein the surface normal is used as a reference of surface normality for the CMM capabilities; and
   a display coupled to said measurement device to facilitate displaying measurements of the machine component.

15. A system in accordance with claim 14, wherein a position of at least one internal defect within the machine component is measured using the UT capabilities.

16. A system in accordance with claim 15, wherein:
   coordinates of the inspection probe are determined using the CMM capabilities; and
   the position of the at least one internal defect is represented with the determined coordinates.

17. A system in accordance with claim 14, wherein said inspection probe is configured to measure a geometry of a rotor blade.

18. A system in accordance with claim 14, wherein said inspection probe is configured to measure a geometry of at least two sides of the machine component when placed in contact with one of the at least two sides.

19. A system in accordance with claim 14, wherein said inspection probe is configured to measure a surface that is substantially normal to the machine component.

20. A system in accordance with claim 14, wherein said display is configured to display the measured external boundaries and the measured internal boundaries in a three-dimensional image.

* * * * *